United States Patent
Engfehr

(10) Patent No.: US 6,580,366 B1
(45) Date of Patent: Jun. 17, 2003

(54) SYSTEM AND METHOD FOR EVALUATING AUTOMOTIVE VEHICLE OIL DETERIORATION

(75) Inventor: John D. Engfehr, Wyandotte, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 09/687,515

(22) Filed: Oct. 13, 2000

(51) Int. Cl.$^7$ ................................ B60Q 1/00
(52) U.S. Cl. .................. 340/457.4; 73/117.3; 340/438; 340/450.3; 701/30
(58) Field of Search ............... 340/450.3, 450, 340/451, 438, 425.5, 457.4, 457; 701/29, 30; 364/550; 73/117.3, 53.05, 54.01, 54.02

(56) References Cited

U.S. PATENT DOCUMENTS

| | | | |
|---|---|---|---|
| 4,506,337 A | 3/1985 | Yasuhara | 73/117.3 |
| 4,533,900 A | 8/1985 | Muhlberger et al. | 73/117.3 |
| 4,706,193 A | 11/1987 | Imajo et al. | 123/196 S |
| 4,742,476 A | 5/1988 | Schwartz et al. | 123/196 S |
| 4,862,393 A * | 8/1989 | Reid et al. | 340/457.4 |
| 4,970,492 A | 11/1990 | King | 340/450.3 |
| 5,060,156 A | 10/1991 | Vajgart et al. | 340/450.7 |
| 5,530,647 A | 6/1996 | Sem et al. | 340/457.4 |
| 5,592,395 A | 1/1997 | Braun et al. | 364/424.035 |
| 5,642,284 A | 6/1997 | Parupalli et al. | 340/438 |
| 5,750,887 A | 5/1998 | Schricker | 340/438 |
| 5,964,256 A * | 10/1999 | Bedi et al. | 123/196 S |
| 6,009,361 A | 12/1999 | Huber et al. | 701/29 |
| 6,037,864 A | 3/2000 | Sem et al. | 340/457.4 |
| 6,043,505 A * | 3/2000 | Ames et al. | 250/577 |
| 6,253,601 B1 * | 7/2001 | Wang et al. | 340/438 |

FOREIGN PATENT DOCUMENTS

DE  195 18 776  11/1996

* cited by examiner

Primary Examiner—Brent A. Swarthout
(74) Attorney, Agent, or Firm—Rader, Fishman & Grauer PLLC; Carlos Hanze

(57) ABSTRACT

A method and system is provided for evaluating the chemical deterioration of automotive engine oil over time. A change in oil quantity is detected and measured by an oil quantity sensor. Based on the change in quantity of oil, the level of chemical deterioration of the oil is inferred.

7 Claims, 3 Drawing Sheets

SYSTEM AND METHOD FOR EVALUATING AUTOMOTIVE VEHICLE OIL DETERIORATION

FIELD OF THE INVENTION

The invention relates generally to a method and system for evaluating chemical deterioration of oil used in automotive internal combustion engines. More specifically, the invention relates to a method and system for evaluating oil deterioration over time based on a change in the quantity of the vehicle's oil.

BACKGROUND OF THE INVENTION

It is well-known that an important aspect of automotive vehicle maintenance includes maintaining good engine lubrication. Because the chemical quality of automotive oil responsible for maintaining good engine lubrication deteriorates over time, good maintenance practices require that the vehicle's oil be changed periodically. Many modern automotive vehicles include among their instrument clusters oil change indicators that notify vehicle operators when it is recommended that the vehicle oil be changed. These vehicles generally include electronic controllers that selectively activate the oil change indicator when it is determined that the vehicle's oil should be changed. Various methods have been used to determine when and under what conditions a vehicle's electronic controller activates the oil change indicator.

One known method is for the controller to activate the oil change indicator when the number of miles that the vehicle has traveled since the last oil change exceeds a certain pre-determined maximum recommended number of miles. For example, the controller might activate the oil change indicator every time the vehicle travels more than 5,000 miles since the previous oil change. Essentially, this method assumes that a vehicle's oil, regardless of the quality of the oil used or the conditions under which the vehicle is operated, deteriorates to an impermissibly low level after such fixed number of miles. Because this method does not consider the quality of the oil used or the vehicle's operating conditions, this method many times results in the oil change indicator being activated even though the vehicle's oil still has remaining useful life.

Another known, and more sophisticated, method involves attempting to directly evaluate the deterioration of the vehicle's oil over time by sensing and measuring a change in electrical conductivity of the vehicle oil over time. Because the conductivity of oil decreases as the chemical qualities of the oil deteriorate, the controller activates the change oil indicator when it determines that the oil's conductivity has fallen to a level that corresponds to an impermissible deterioration of the oil quality. This method is limited in its usefulness at least because (i) the conductivity sensor cannot detect the initial quality of different types of oil; (ii) oil that is added between complete oil changes must be of the same initial quality as the original oil; and (iii) excessive data "noise" in sensing the electrical conductivity makes the method relatively inaccurate. With respect to the data "noise" limitation, it is known that the occurrence of water condensation in the oil changes the overall conductivity of the oil significantly, which leads to inaccurate conclusions regarding the quality of the oil. Accordingly, this method has not been effectively used in production.

Yet another known method involves indirectly estimating the deterioration of the vehicle oil over time based on a variety of vehicle operating data, such as total engine RPMs, total number of cold starts, time interval since previous oil change, etc. Recognizing that different driving conditions result in the deterioration of oil quality at different rates, this method applies complex models and algorithms to the measured vehicle operating data to estimate the rate of oil quality deterioration. This method is limited at least because it requires that several operational data be sensed and stored in system memory, and the algorithms for estimating the oil degradation are complex.

Accordingly, there is a need for a simpler and more accurate system and method for evaluating the quality of a vehicle's oil.

SUMMARY OF THE INVENTION

The present invention generally relates to a new method to evaluate the quality of a vehicle's oil that is both more accurate and more efficient to implement than existing methods and systems. Based on the oil quality evaluation, the vehicle's electronic controller selectively activates either an "oil change" indicator or a "low oil" indicator in the vehicle's instrument cluster to provide appropriate maintenance information to the vehicle operator.

The inventor hereof has discovered that oil consumption in an internal combustion engine increases significantly after the chemical quality of the oil deteriorates past a certain point. As a result, when the oil quality sufficiently deteriorates, the quantity of the oil in the system falls significantly. FIG. 1A generally illustrates the inventor's empirical observation that oil quantity in an internal combustion engine generally decreases over time as a result of operation. FIG. 1B generally illustrates the inventor's empirical observation that oil quality (measured in terms of Total Base Number (TBN)) tends to deteriorate over time as a result of operation. The inventor has discovered that a useful correlation exists between the amount of oil consumption and the quality of the remaining oil in the system. Specifically, oil is consumed by the engine much more rapidly once the oil's quality deteriorates past a certain point. The present invention uses the correlation between oil consumption (loss of oil quantity) and oil quality deterioration to evaluate the chemical quality of a vehicle's oil over time and to signal the vehicle operator as to when it is appropriate to either add oil or completely change the vehicle's oil.

An oil quantity sensor, preferably positioned in the vehicle's oil pan, detects the oil quantity in the vehicle's oil system. When the oil quantity sensor detects that the oil level in the oil system has fallen to a certain low oil reference value, the controller selectively activates either a "change oil" indicator or "low oil" indicator based on the change in oil quantity and certain oil maintenance parameters indicative of the driving conditions under which the vehicle has been operated.

DESCRIPTION OF A PREFERRED EMBODIMENTS

Figure 1A:
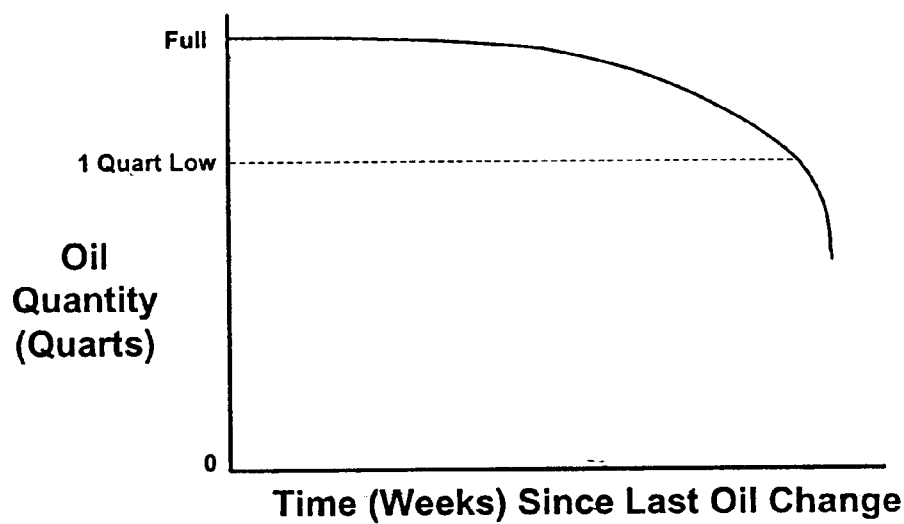
FIG. 1A is a graph illustrating the decrease in oil quantity over time.
Figure 1B:
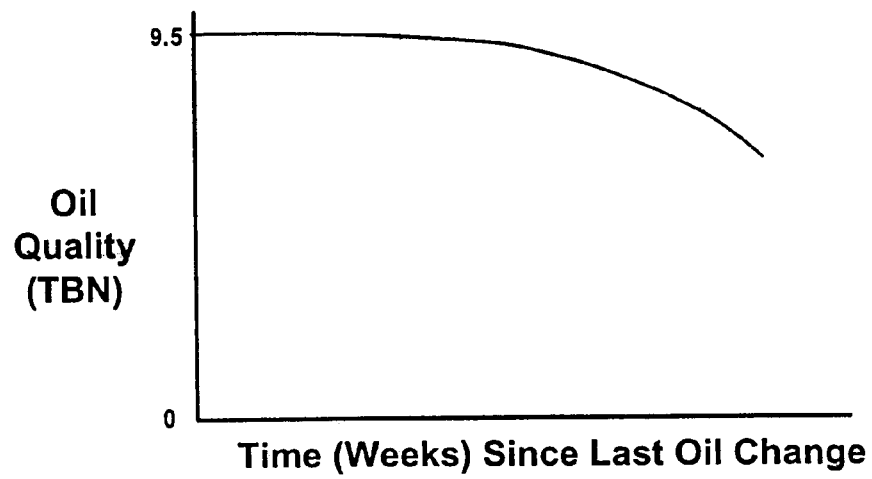
FIG. 1B is a graph illustrating the deterioration of oil quality over time.
Figure 2:
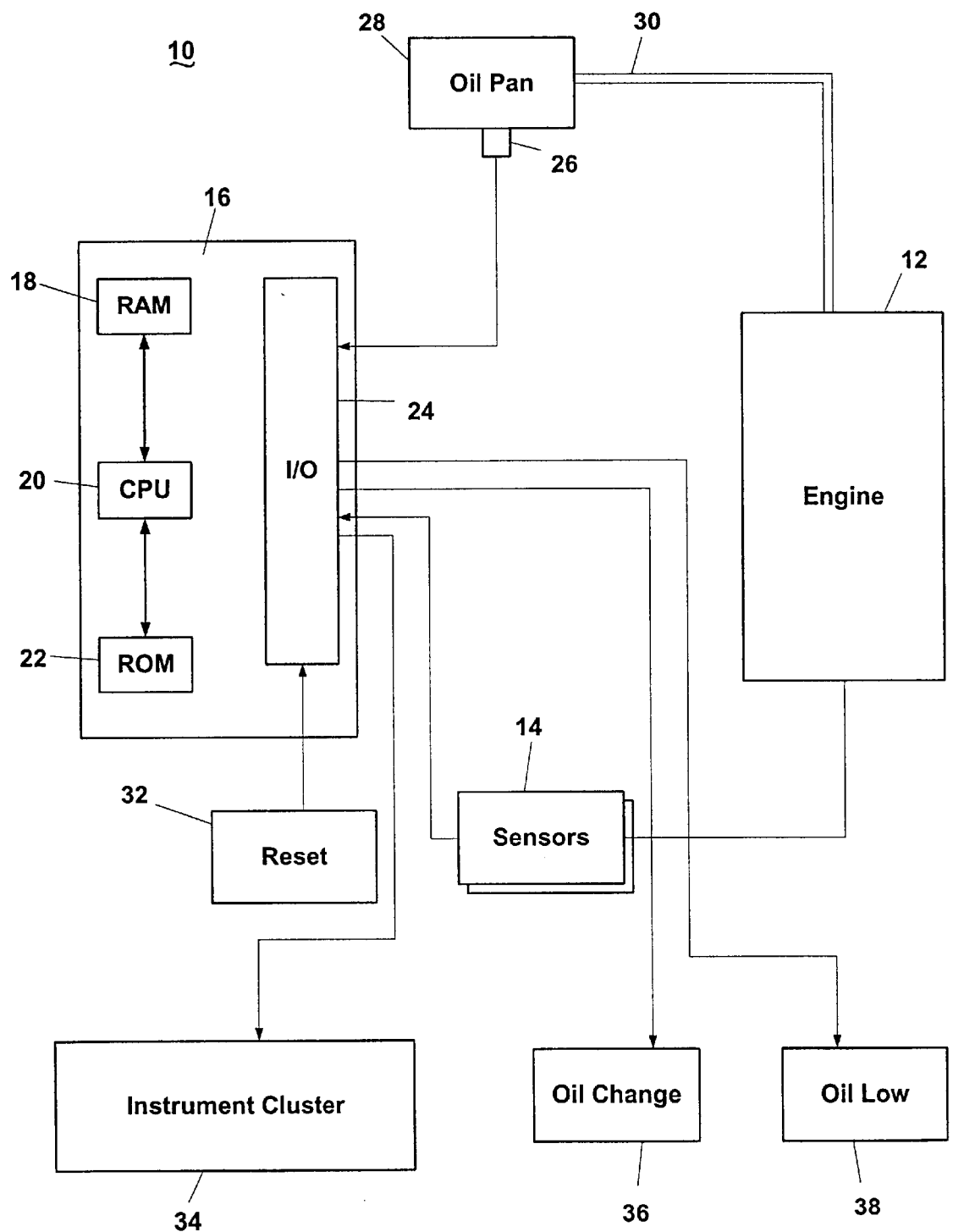
FIG. 2 is a block diagram illustrating the functional relationship of the vehicle's engine, oil pan, sensors, and electronic controller, according to a preferred embodiment of the invention.

FIG. 2 is a block diagram that generally illustrates the functional system 10 of a preferred embodiment of the invention. Various engine sensors 14 are coupled to engine 12 to detect a variety of operational parameters. Sensors 14 provide corresponding electronic signals to instrument cluster controller 16. Instrument cluster controller 16 is a conventional electronic controller that includes random access memory (RAM) 18, central processing unit (CPU) 20, read only memory (ROM) 22, an input/output data bus 24. Generally, controller 16 uses the input signals from sensors 14 to control the outputs of the vehicle's instrument cluster 34. Two components of the vehicle's instrument cluster that are shown separately in FIG. 2 are "oil change" indicator 36 and "oil low" indicator 38, which are selectively activated by controller 16 according to the invented method.

Oil pan 28 stores the oil system's oil. Oil is provided to the engine 12 from the oil pan 28 via oil duct 30. Oil quantity sensor 26 is coupled to oil pan 28 for sensing the quantity of oil in the oil pan 28 and providing an indicative electronic signal to controller 16. Oil change reset mechanism 32 provides an electronic signal to controller 16 to indicate when the oil in the vehicle has been completely changed. In the preferred embodiment of the invention, oil change reset mechanism 32 is a manual switch or button that is manually activated by the vehicle operator when the oil has been completely changed. In other embodiments of the invention, the oil change reset mechanism 32 could be any mechanism, such as an automatic sensor and the like, that provides an indication that the vehicle's oil has been completely changed.

The present invention generally includes using the information from oil quantity sensor 26 relating to the change in oil quantity over time to provide oil maintenance information to the vehicle operator. However, oil consumption occurs not only as a result of chemical deterioration, but also as a normal result of the mechanical operation of the vehicle. The normal rate of oil consumption prior to significant chemical deterioration of the oil varies according to driving conditions. That is, the quantity of the vehicle's oil may fall over the course of an oil change interval (elapsed time between oil changes) even though the chemical qualities of the oil may still be suitable for providing sufficient lubrication to the engine. Therefore, though the present invention could be employed such that the oil change indicator 36 was activated whenever the quantity of the oil decreased to a certain low oil reference value, it is desirable in the preferred embodiment of the invention to combine the information derived from the change in oil quantity with other parameters indicative of the vehicle driving conditions to evaluate the chemical deterioration of the oil. Examples of such parameters include the time and distance since the prior oil change and the relative oil consumption rates over time. Based on this combination of data, the controller 16 selectively activates the "oil change" indicator 36 or the "oil low" indicator 38.

It is known that the rate of normal mechanical oil consumption by an internal combustion engine varies depending on the driving conditions under which the vehicle is operated. For example, under severe driving conditions, such as continuous high-speed and/or highload operation, normal mechanical oil consumption will likely be relatively high, though the chemical deterioration of the oil will be relatively minimal. Therefore, to fully utilize the life of the vehicle's oil, it may be desirable to simply add additional oil to the oil system instead of changing the oil completely. On the other hand, when the vehicle is used primarily for short trips wherein the engine operating temperature remains relatively low ("short trip" cycle operation), fuel and water condensation contamination of the oil may actually cause the measured oil quantity to rise above the "full" level. Under these circumstances, the chemical deterioration of the oil may reach an unacceptable level before the fall in oil quantity reaches the low oil reference value. Accordingly, under these driving conditions, it may be desirable to activate the "oil change" indicator before the oil level reaches the low oil reference value. Finally, under normal driving conditions (i.e., a combination of long and short trips and a combination of city and highway driving), it is possible to extend the useful life of the vehicle's oil after it falls to the low oil reference value by "topping off" the oil pan. The new oil used to "top off" the oil pan will increase the overall integrity of the vehicle's oil supply, thereby extending its useful life. Accordingly, it may be economical for the vehicle operator, as well as ecologically sound for the environment, to "top off" the oil pan a certain number of times, depending on the driving conditions, instead of completely changing the oil each time the oil quantity falls to the low oil reference value.

The preferred embodiment of the present invention uses three oil maintenance parameters, in combination with change in quantity information, to estimate the driving conditions to which the vehicle has been subjected during the current oil change interval. Specifically, the preferred three oil maintenance parameters comprise (i) the elapsed time since the last oil change, (ii) the driving distance since the last oil change, and (iii) the driving distance since the last "low oil" determination within the current oil change cycle (a "low oil interval"). Other embodiments of this invention may use other oil maintenance parameters that are indicative of various driving conditions. Using the preferred oil maintenance parameters, the ratio of the driving distance in miles to the elapsed time in months since the last oil change (the "distance to elapsed time ratio") is below a certain reference value, preferably about 250, then it is estimated that the vehicle has been operated in a Short Trip Cycle. Similarly, if the oil quantity is above a "full" level after a certain elapsed time since the last oil change, preferably about six months, then it is also estimated that the vehicle has been operated in a Short Trip Cycle. On the other hand, if the oil quantity falls to the low oil reference value and the low oil interval is approximately equal to or greater than the previous low oil interval within the same oil change cycle, then it is estimated that the vehicle has been operated under severe conditions. If the oil quantity falls to the low oil reference value and the low oil interval is less than the previous low oil interval within the same oil change cycle (interval between oil changes), then it is estimated that the vehicle has been operated under normal conditions. From these estimations of driving conditions, in combination with the change in oil quantity information, the controller 16 selectively activates the "low oil" and "change oil" indicators.

Figure 3:
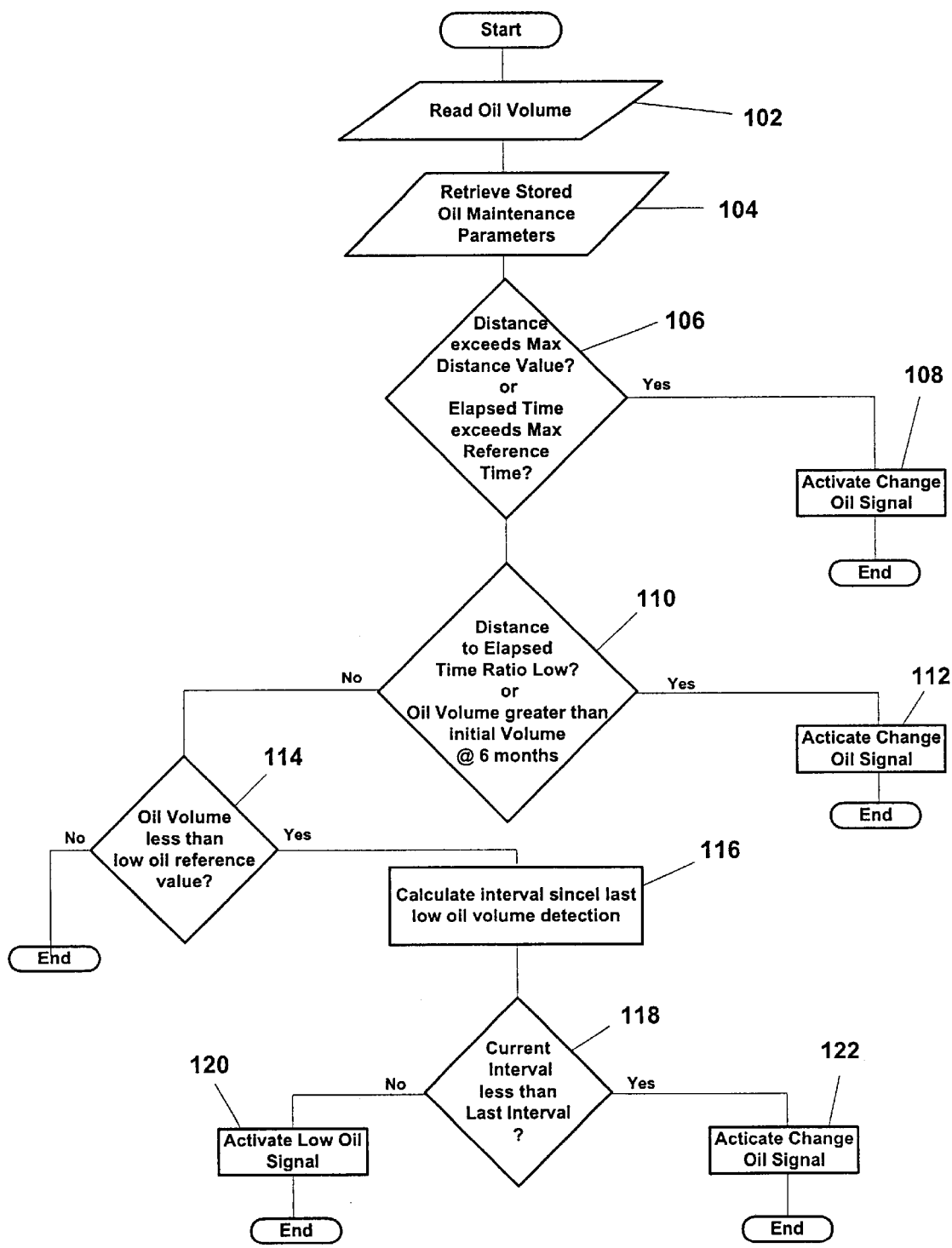
FIG. 3 is a flowchart illustrating steps of the invented method, according to a preferred embodiment of the invention.

Referring now to FIG. 3, a preferred embodiment of the present invented method will be described in more detail. First, as shown in block 102, the oil quantity sensor 26 detects the oil quantity in the oil pan 28. To ensure accuracy of the measurement, this step preferably occurs when the engine is not running. Therefore, this step is preferably executed either after the engine has been turned off for a reasonable amount of time or just after the vehicle key has been inserted into the ignition but before the engine is actually started.

Second, as shown in block 104, the oil maintenance parameters, as described above, are retrieved from the controller's RAM 18. These values are updated and/or reset in the controller's RAM each time the vehicle's oil reset mechanism 32 indicates that the oil has been changed or when the oil level sensor detects that the oil quantity has fallen to the low oil reference value, as appropriate. All three parameters are reset to zero each time the reset mechanism 32 is activated, and the low oil interval parameter is updated each time oil is added to the oil pan during an oil change cycle.

Next, as shown in block 106, the controller determines whether either the distance or the elapsed time since the last oil change exceeds a corresponding maximum reference value. In the preferred embodiment, the maximum distance reference value is about 12,500 miles and the maximum oil change interval reference value is about one year. If either of these conditions is true, then the controller activates the "oil change" indicator, as shown in block 108. These conditions are essentially catch-all conditions that prevent the possibility that a combination of different driving conditions may "fool" the system into indicating a permissible oil quality when it has actually deteriorated to an impermissible level.

If neither of the catch-all conditions apply, then the controller 16 determines (block 110) if either (i) the distance (in miles) to elapsed time ratio (in months) is too low, preferably below about 250, or (ii) the oil quantity has increased above the "full" or initial oil level and the elapsed time since the previous oil change exceeds a maximum value, preferably six months. The preferred "full" or initial oil level is about five quarts. If either of these conditions apply, then it is estimated that the vehicle has been operated in a Short Trip Cycle, and the controller activates the "change oil" indicator 36, as shown in block 112.

As shown in block 114, if neither of the Short Trip Cycle conditions apply, then the controller compares the measured oil quantity to the low oil reference value. In the preferred embodiment of the invention, the low oil reference value is about four quarts, or one quart below the preferable "full" or initial oil level. If the measured oil quantity is equal to or less than the low oil reference value, it is determined that the vehicle is in a low oil condition. It should be noted that the invented method would function equivalently if the measured oil quantity were compared to the initial oil quantity instead of a low oil reference value. In this case, the method would compare the change in oil quantity to a reference quantity to estimate the level of oil quality deterioration.

In the preferred embodiment of the invention, if the measured oil quantity is greater than the low oil reference value, then no action relative to the "oil change" or "low oil" indicators is taken. However, if the measured oil quantity is equal to or less than the low oil reference value, then the controller calculates the current low oil detection interval, i.e., the elapsed time since the previous low oil condition was detected. This is shown in block 116. Based on the low oil detection interval, the controller estimates the driving conditions under which the vehicle has been operated and selectively activates the appropriate oil maintenance indicator accordingly. Specifically, as shown in block 118, the controller compares the current low oil detection interval to the previous low oil detection interval. If the current low oil detection interval is approximately equal to or greater than the previous low oil detection interval, then it is determined that the useful life of the current oil supply can be extended by simply adding additional new oil to the oil pan. Accordingly, the controller activates the "low oil" indicator, as shown in block 120. On the other hand, if the current low oil detection interval is approximately less than the previous low oil detection interval, then it is determined that the useful life of the existing oil supply cannot or should not be extended. Therefore, the controller activates the "change oil" indicator, as shown in block 122.

According to the above-described preferred embodiment of the invented method, the relative lengths of consecutive low oil detection intervals are determinative of whether the vehicle operator is instructed to completely change the vehicle's oil or merely add additional new oil to the reservoir. Because the previous low oil detection interval parameter is reset to zero each time the oil is completely changed, the first time in each oil change cycle that the measured oil level falls below the low oil reference level, the current low oil detection interval will always be greater than the previous low oil detection interval. Accordingly, under either normal or severe driving conditions, the controller will always activate the "low oil" indicator at least once, provided that neither of the catch-all conditions (block 106) apply before the oil level falls to the low oil reference level. When the vehicle is primarily subjected to severe driving conditions, the rate of normal mechanical oil consumption will likely outpace the rate of consumption due to chemical deterioration. Under these conditions, each time the measured oil level falls below the low oil reference level, the current low oil detection interval will likely be approximately equal to the previous low oil detection interval. Therefore, under continuous severe driving conditions, the preferred embodiment of the invention will instruct the vehicle operator to add oil to the system, instead of completely changing the oil, until one of the catch-all conditions become true. On the other hand, when the vehicle is primarily operated under normal conditions or a combination of normal and severe conditions, oil consumption due to chemical deterioration will likely outpace normal mechanical oil consumption. Under these conditions, the second low oil detection interval will likely be significantly less than the first low oil detection interval. Therefore, normal driving conditions will result in an indication that the oil should be completely changed upon the second time the oil quantity falls below the low oil reference value.

While preferred embodiments of the present invention have been described herein, it is apparent that the basic construction can be altered to provide other embodiments that utilize the processes and compositions of this invention. Therefore, it will be appreciated that the scope of this invention is to be defined by the claims appended hereto rather than by the specific embodiments that have been presented hereinbefore by way of example.

What is claimed is:

1. In an automotive vehicle, a method for evaluating automotive oil deterioration, comprising the steps:

determining an oil quantity in the vehicle;

comparing said oil quantity to an oil quantity reference value;

calculating a low oil detection interval comprising an elapsed time or elapsed distance since a previous detection of a low oil condition; and determining that the oil has deteriorated to a significant level when (i) said oil quantity is less than said oil quantity reference value, and (ii) a current low oil detection interval is less than a previous low oil detection interval.

2. The method of claim 1, wherein it is further determined that said oil deterioration has progressed to a significant level when (i) a distance traveled by the vehicle since a previous oil change is low relative to an elapsed time since a previous oil change, or (ii) said oil quantity is greater than an initial oil quantity and said elapsed time since a previous oil change is greater than a maximum oil change interval reference value.

3. In an automotive vehicle, a method of indicating automotive oil maintenance information, comprising the steps:

measuring a plurality of oil quantities in the vehicle over time;

comparing each of said oil quantities to an oil quantity reference value;

calculating a first elapsed time between a previous oil change and a first instance when a first of said oil quantities is less than said oil quantity reference value;

calculating a second elapsed time between said first instance and a subsequent instance when a second of said oil quantities is less than said oil quantity reference value; and indicating that the automotive oil should be changed if said second oil quantity is approximately less than said oil quantity reference value and said second elapsed time is approximately less than said first elapsed time.

4. The method of claim 3, further comprising the step of indicating that additional oil should be added to the existing oil in the vehicle if said current oil quantity is approximately less than said oil quantity reference value and said second elapsed time is approximately equal to or greater than said first elapsed time.

5. The method of claim 4, further comprising the steps:

calculating an elapsed driving distance since a previous oil change;

calculating an elapsed time since said previous oil change;

indicating that the automotive oil should be changed if said elapsed driving distance is low relative to said elapsed time and said current oil quantity is approximately greater than said initial oil quantity.

6. The method of claim 5, further comprising the step of indicating that the automotive oil should be changed if said elapsed time since said previous oil change exceeds a maximum oil change interval reference value or if said elapsed driving distance exceeds a maximum distance reference value.

7. The method of claim 6, wherein said indicating step comprises selectively activating at least one sensory indicator inside of the vehicle.

* * * * *